(12) United States Patent
Spano (10) Patent No.: US 10,245,051 B2
(45) Date of Patent: Apr. 2, 2019

(54) DRUG DELIVERY VIA MECHANICAL VIBRATION BALLOON (71) Applicant: BARD PERIPHERAL VASCULAR, Tempe, AZ (US)

(72) Inventor: Richard Samuel Spano, Gilroy, CA (US)

(73) Assignee: Bard Peripheral Vascular, Inc., Franklin Lakes, NJ (US)

(*) Notice: Subject to any disclaimer, the term of this patent is extended or adjusted under 35 U.S.C. 154(b) by 58 days.

(21) Appl. No.: 14/758,557

(22) PCT Filed: Dec. 20, 2013

(86) PCT No.: PCT/US2013/077232
§ 371 (c)(1),
(2) Date: Jun. 29, 2015

(87) PCT Pub. No.: WO2014/105754
PCT Pub. Date: Jul. 3, 2014

(65) Prior Publication Data
US 2015/0343191 A1 Dec. 3, 2015

Related U.S. Application Data (60) Provisional application No. 61/746,807, filed on Dec. 28, 2012.

(51) Int. Cl.
A61B 17/22 (2006.01)
A61M 25/10 (2013.01)
(Continued)

(52) U.S. Cl.
CPC ....... *A61B 17/22012* (2013.01); *A61M 25/10* (2013.01); *A61M 37/0092* (2013.01);
(Continued)

(58) Field of Classification Search
CPC .............. A61M 25/10; A61M 37/0092; A61M 2025/105; A61M 2025/1031;
(Continued)

(56) References Cited

U.S. PATENT DOCUMENTS 4,217,786 A * 8/1980 Okude ................... G10K 11/24
116/137 A
4,901,729 A * 2/1990 Saitoh ................... G10K 11/02
310/336

(Continued)

FOREIGN PATENT DOCUMENTS

DE 10146011 A1 4/2003
WO 9401047 A1 1/1994
(Continued)

Primary Examiner — Bradley J Osinski
Assistant Examiner — Nilay J Shah (57) ABSTRACT A drug coated inflatable balloon catheter (200) configured to vibrate is disclosed. The vibration can dislodge the drug from the balloon. The vibration can also improve delivery of the drug to deeper layers of a vessel wall. The balloon catheter can include one or more support wires. The support wires can be coupled to an ultrasound transmission member (120). The ultrasound transmission member can transmit ultrasonic vibrations to the support wires and/or the balloon wall.

15 Claims, 8 Drawing Sheets (51) Int. Cl.
*A61M 37/00* (2006.01)
*A61B 17/32* (2006.01)

(52) U.S. Cl.
CPC .............. *A61B 17/320068* (2013.01); *A61B 2017/22014* (2013.01); *A61B 2017/22039* (2013.01); *A61B 2017/22061* (2013.01); *A61M 2025/105* (2013.01); *A61M 2025/109* (2013.01); *A61M 2025/1084* (2013.01)

(58) Field of Classification Search
CPC ........ A61B 17/320068; A61B 17/3207; A61B 17/12022; A61F 2/95; A61F 2/954; A61F 2002/9586; A61F 2/958
See application file for complete search history.

(56) References Cited

U.S. PATENT DOCUMENTS

| | | | |
|---|---|---|---|
| 4,961,424 A * | 10/1990 | Kubota | A61B 17/22012 601/2 |
| 5,267,954 A | 12/1993 | Nita | |
| 5,722,979 A * | 3/1998 | Kusleika | A61B 17/22012 604/22 |
| 5,989,208 A | 11/1999 | Nita | |
| 6,007,514 A | 12/1999 | Nita | |
| 6,427,118 B1 | 7/2002 | Suzuki | |
| 6,702,748 B1 | 3/2004 | Nita et al. | |
| 6,855,123 B2 | 2/2005 | Nita | |
| 6,942,620 B2 | 9/2005 | Nita et al. | |
| 6,942,677 B2 | 9/2005 | Nita et al. | |
| 7,137,963 B2 | 11/2006 | Nita et al. | |
| 7,153,315 B2 | 12/2006 | Miller | |
| 7,220,233 B2 | 5/2007 | Nita et al. | |
| 7,297,131 B2 | 11/2007 | Nita | |
| 7,335,180 B2 | 2/2008 | Nita et al. | |
| 7,393,338 B2 | 7/2008 | Nita | |
| 7,540,852 B2 | 6/2009 | Nita et al. | |
| 7,604,608 B2 | 10/2009 | Nita et al. | |
| 7,803,149 B2 | 9/2010 | Bates et al. | |
| 7,901,378 B2 | 3/2011 | Solar et al. | |
| 7,951,111 B2 | 5/2011 | Drasler et al. | |
| 8,133,236 B2 | 3/2012 | Nita | |
| 8,226,566 B2 | 7/2012 | Nita | |
| 8,246,643 B2 | 8/2012 | Nita | |
| 2004/0073284 A1 * | 4/2004 | Bates | A61F 2/82 623/1.11 |
| 2004/0249401 A1 | 12/2004 | Rabiner et al. | |
| 2012/0215099 A1 | 8/2012 | Wallace | |

FOREIGN PATENT DOCUMENTS

| | | |
|---|---|---|
| WO | 0160441 A1 | 8/2001 |
| WO | 2011094379 A1 | 8/2011 |
| WO | 2012151048 A2 | 11/2012 |
| WO | 2014105754 A1 | 7/2014 |

* cited by examiner

DRUG DELIVERY VIA MECHANICAL VIBRATION BALLOON

CROSS-REFERENCE TO RELATED APPLICATIONS

This application is a U.S. national stage application under 35 U.S.C. § 371 of International Application No. PCT/US2013/077232, filed Dec. 20, 2013, which claims priority under 35 U.S.C. § 119(e) to U.S. Provisional Application No. 61/746,807, filed Dec. 28, 2012, entitled "DRUG DELIVERY VIA MECHANICAL VIBRATION BALLOON," which are hereby incorporated by reference in their entirety.

BACKGROUND OF THE INVENTION

Field of the Invention

This disclosure generally relates to a device, system, and method for treating obstructed vessels. More particularly, the disclosure relates to systems and devices that include an inflatable drug coated balloon catheter configured to vibrate and methods of use.

Description of the Related Art

There are many procedures and systems for treating vascular or venous obstructions that are occluded with atheroma, plaque, calcific material, and the like. Such obstructions are often referred to as vascular occlusions. Partial and total occlusions can be treated, for example, by a surgical bypass procedure or a catheter-based intervention such as angioplasty, balloon angioplasty, stenting, and the like.

Ultrasound systems and devices have been proposed for use in ablating or removing obstructive material from blood vessels. Ultrasound catheters have been utilized to ablate various types of obstructions from blood vessels of humans and animals. Successful applications of ultrasound energy to smaller blood vessels, such as the coronary arteries, require the use of relatively small diameter ultrasound catheters which are sufficiently small and flexible to undergo transluminal advancement through the tortuous vasculature of the aortic arch and coronary tree. These ultrasound catheters incorporate a very small diameter ultrasound transmission member which extends through such catheters.

SUMMARY OF THE INVENTION

The devices and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of Certain Preferred Embodiments" one will understand how the features of this invention provide several advantages over traditional procedures relating to the treatment of vascular and/or venous occlusions.

BRIEF DESCRIPTION OF THE DRAWINGS

FIGS. 3D' and 3D" are cross-sectional views of the drug delivery balloon shown in FIG. 3A taken along line 3D-3D according to alternate embodiments.

DETAILED DESCRIPTION OF CERTAIN PREFERRED EMBODIMENTS

The following description and the accompanying figures describe and show the preferred embodiments as well as demonstrate several possible configurations for a mechanical vibration drug delivery balloon, system, and methods of use. The illustrations are not intended to limit the disclosed aspects and features of the invention to the specified embodiments or to usage only with the illustrated devices. Those of skill in the art will recognize that the disclosed aspects and features of the invention are not limited to any particular embodiment of a mechanical vibration drug delivery balloon, which may include one or more of the inventive aspects and features described herein.

Percutaneous transluminal angioplasty ("PTA") and percutaneous transluminal coronary angioplasty ("PTCA") may be used to open stenotic or occluded vessels. In general, a balloon is placed in the stenotic segment of the vessel and then expanded. The expanded balloon re-opens the vessel lumen. The balloon is then deflated and removed. A stent may be implanted. However, elastic recoil and restenosis often occurs after such procedures.

Stents, drug-eluting stents, drug-eluting balloons, and the like may help prevent restenosis. Drug-eluting stents and balloons can deliver drugs and/or therapeutics to the vessel wall which can help prevent restenosis. The effectiveness of drug-eluting balloons often depends on the pressure with which the balloon is inflated and/or the length of time the inflated balloon contacts the vessel wall.

According to the present invention, a drug-eluting or drug-coated balloon can increase the effectiveness of drug delivery to the sub-layers of the vessel wall. The systems, methods, and devices disclosed herein enable the increased delivery of a therapeutic to the target area (i.e. the vessel wall). In some embodiments, ultrasound energy is used to vibrate a drug-coated balloon. The drug-coated balloon may be inflated to contact the interior walls of a vessel in need of treatment. The drug-coated balloon may be coupled with a mechanical vibration transmission wire. The drug-coated balloon may then be vibrated. The vibration can increase the amount of drug transmitted from the surface of the balloon to the interior of the vessel walls, thus increasing the effectiveness of the treatment and further preventing restenosis. The drug coating may be paclitaxel. In sum, the systems, devices, and methods disclosed herein provide for a drug-coated balloon to be longitudinally vibrated at ultrasonic frequencies in order to deliver anti-stenosis drugs such as paclitaxel to deeper cellular layers in the vessel.

To assist in the description of these components of the systems, methods, and devices disclosed herein, the following coordinate terms are used. A "longitudinal axis" is generally parallel to a portion of the drug delivery balloon device as well as parallel to the axis of a vessel through which the drug delivery balloon device can travel. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the drug delivery balloon device, and therefore is substantially synonymous with the term "longitudinal" as used herein. Also, the terms "proximal" and "distal," which are used to describe the present system, are used consistently with the description of the exemplary applications (i.e., the illustrative examples of the use applications). Thus, proximal and distal are also used in reference to the respective ends of the drug delivery balloon device.

To facilitate a complete understanding of the embodiments, the remainder of the detailed description describes the drug delivery balloon systems, methods, and devices, with reference to the Figures; wherein like elements among the embodiments are referenced with like numerals throughout the following description.

Figure 1:
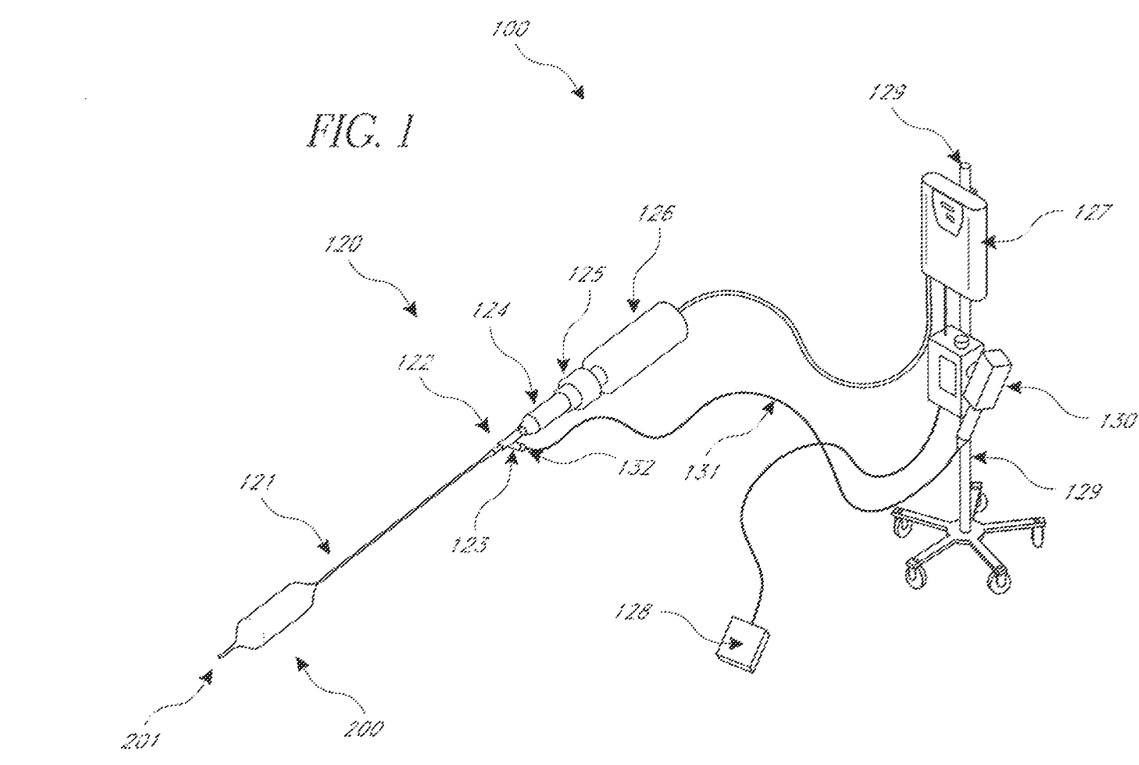
FIG. 1 is a perspective view of an ultrasound system including a drug delivery balloon that can be used to treat vascular or venous occlusions according to a preferred embodiment of the present invention.

FIG. 1 shows an example of a perspective view of an ultrasound system 100 that can be used with drug delivery balloon 200. The ultrasound system 100 includes an ultrasound device 120 which is releasably coupled to an ultrasound transducer 126. The distal end of the ultrasound device 120 includes the drug delivery balloon 200.

The ultrasound transducer 126 is electrically coupled to a signal generator 127. The ultrasound device 120 may include an elongate body having a proximal portion 122 and a distal portion 121. The ultrasound device 120 may be an ultrasonic energy delivery member, or a catheter having at least one lumen extending longitudinally with an ultrasound transmission member extending therethrough.

The signal generator 127 can send electrical signals to the ultrasound transducer 126. The ultrasound transducer 126 can then convert the electrical signals to ultrasonic vibrations. The ultrasonic vibrations can then be transmitted through the ultrasound transmission member and the drug delivery balloon, thus delivering ultrasonic vibrations to a treatment location. In some embodiments, ultrasonic vibrations are longitudinal ultrasonic vibrations. The treatment location can be an area of a vessel and/or vessel wall that has stenosis or restenosis. Vessels can include veins and arteries. The methods and devices described herein can also be applied to other body lumens and organs, for example, biliary ducts.

The ultrasound device 120 may also include a Y-connector 123 that is operatively coupled to the ultrasound transducer 126. For example, the Y-connector 123 may be coupled to the ultrasound transducer 126 by way of a device knob 124 and a slide collar 125. The ultrasound transducer 126 may be connected to a signal generator 127, which may be coupled to a foot actuated on-off switch 128. The signal generator 127 can be supported by an IV pole 129. When the on-off switch 128 is depressed, the signal generator 127 can send an electrical signal to the ultrasound transducer 126, which converts the electrical signal to ultrasound energy. Such ultrasound energy can subsequently pass through the ultrasound device 120 and be delivered to the distal portion 121. A conventional guidewire (not shown) may be utilized in conjunction with the device 120.

Continuing with FIG. 1, the frontal portion of the Y-connector 123 may be connected to the proximal end 122 of the ultrasound device 120 using techniques that are well-known in the art. An injection pump 130 or IV bag (not shown) or syringe (not shown) may be connected, by way of an infusion tube 131, to an infusion port or sidearm 132 of the Y-connector 123. The injection pump 130 can be used to infuse coolant fluid into and/or through the device 120. Such flow of coolant fluid may be utilized to prevent overheating of the ultrasound transmission member and may serve to bathe the outer surface of the ultrasound transmission member, thereby providing for an equilibration of temperature between the coolant fluid and the ultrasound transmission member. The temperature and/or flow rate of coolant fluid may be adjusted to provide adequate cooling and/or other temperature control of the ultrasound transmission member. The irrigation fluid can include a pharmacological agent and/or microbubbles. The pharmacological agent may help prevent re-stenosis. In addition to the foregoing, the injection pump 130 or syringe may be utilized to infuse a radiographic contrast medium into the device 120 for purposes of imaging. Examples of iodinated radiographic contrast media which may be selectively infused into the ultrasonic device 120 via the injection pump 130 are commercially available as Angiovist 370 from Berlex Labs, Wayne, N.J. and Hexabrix from Malinkrodt, St. Louis, Mo. The injection pump 130 or syringe may be used to inflate and/or deflate the drug delivery balloon 200.

Generally, the ultrasonic device 120 may include any suitable number of side-arms or ports for passage of a guidewire, application of suction, infusing and/or withdrawing irrigation fluid, dye and/or the like, or any other suitable ports or connections. Also, the device may be used with any suitable ultrasound transducer 126, signal generator 127, coupling device(s) and/or the like. Therefore, the exemplary embodiment shown in FIG. 1 and any following descriptions of proximal apparatus or systems for use with ultrasound devices 120 should not be interpreted to limit the scope of the present invention as defined in the appended claims.

Figure 2A:
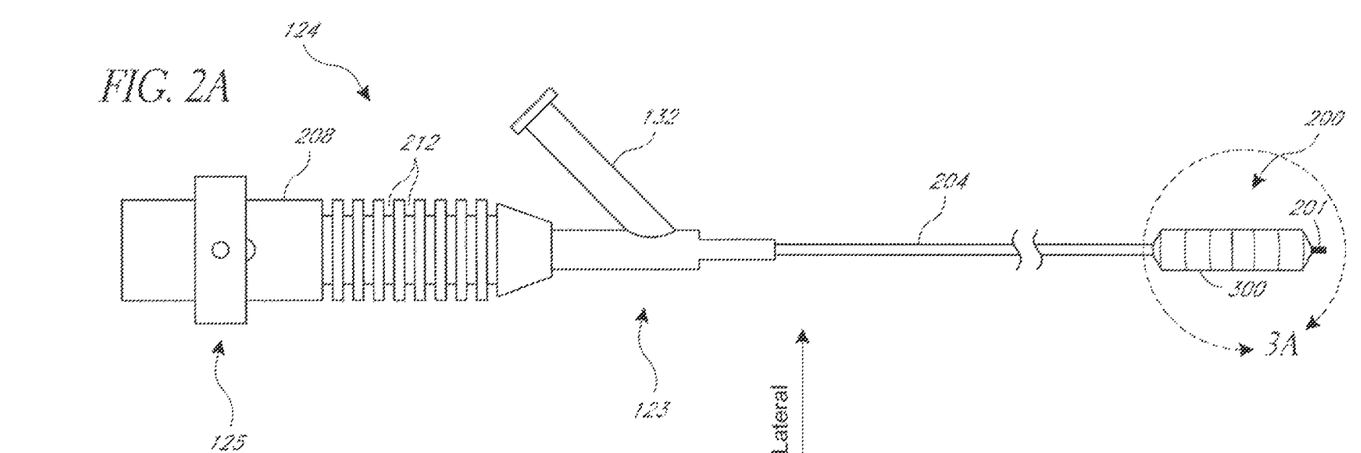
FIG. 2A is a side view of the ultrasound device including the drug delivery balloon shown in FIG. 1.

FIG. 2A is a side view of the ultrasound device including the drug delivery balloon 200 shown in FIG. 1. As illustrated, the distal portion of the Y-connector 123 is coupled to a catheter body 204. The ultrasound transmission member 230 can pass through the device knob 124, Y-connector 123, catheter body 204, and delivery balloon 200.

The device knob 124 can include a proximal housing 208. The housing 208 may include one or more surface features 212 for increasing the outer surface area of housing 208. Increased surface area can enhance the ability of housing 208 to dissipate heat generated by ultrasound transmission member 230. Surface features 212 may be of any suitable size or shape and can include, for example, ridges, jags, undulations, grooves or the like. Any suitable number of surface features 212 may be used. Additionally, the housing 208 may be made of one or more heat dissipating materials, such as aluminum, stainless steel, any other conductive metal(s), or any suitable non-metallic conductive material.

Continuing with FIG. 2A, the Y-connector 123 can be coupled to the catheter body 204. The catheter body 204 can be coupled to the drug delivery balloon 200. The Y-connector 123 can be coupled to the catheter body 204 by any coupling manner well known in the art and in some embodiments is fixably attached.

The catheter body 204 may be a generally flexible, tubular, elongate member, having any suitable diameter and length for reaching a vascular occlusion. In some embodiments, for example, the catheter body 204 has a length in the range of about 100-200 cm. In one embodiment, the catheter body 204 has an outer diameter in the range of about 0.5-5.0 mm. In other embodiments, for use in relatively small vessels for example, the catheter body 204 may have an outer diameter in the range of about 0.25-2.5 mm. However, any other suitable length or diameter may be used without departing from the scope of the present invention. Examples of catheter bodies similar to those which may be used in the present invention are described in U.S. Pat. Nos. 5,267,954 and 5,989,208, which are herein incorporated by reference in their entireties. The catheter body 204 can insulate the ultrasound transmission member 230 and prevent an operator's hands from contacting the ultrasound transmission member 230 during use of the device. The catheter body 204 can also serve as an inflation lumen for the drug delivery balloon 200.

Figure 2B:
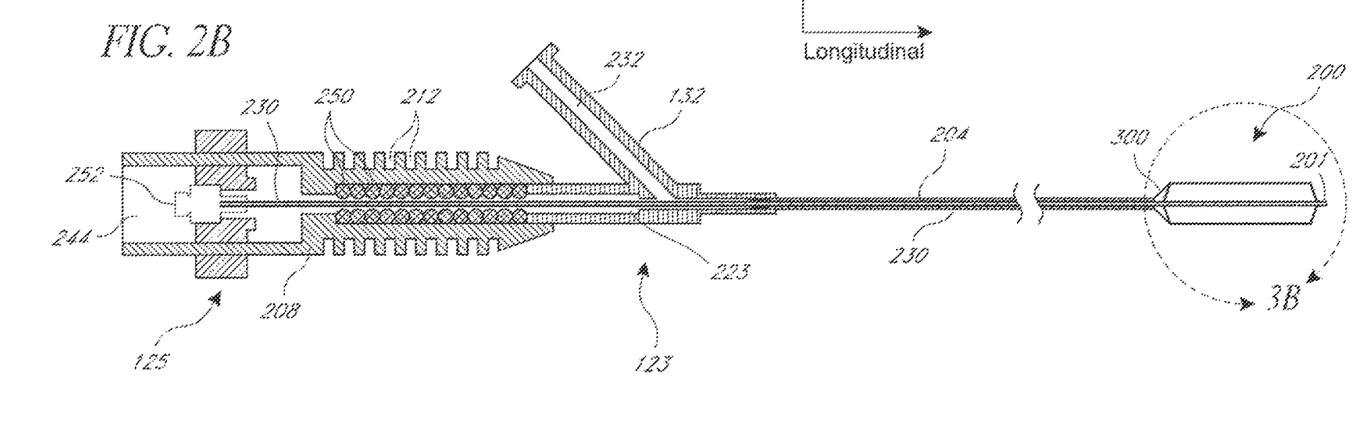
FIG. 2B is a cross-sectional view of the ultrasound device including the drug delivery balloon shown in FIG. 2A.

FIG. 2B shows a cross-sectional view of the ultrasound device 120 device including the drug delivery balloon 200. As depicted, the housing 208 can include an inner cavity 244. Disposed within the cavity 244 is a sonic connector 252. The ultrasound transmission member 230 extends in a distal direction from the sonic connector 252 and through the cavity 244.

The inner cavity 244 may include one or more vibration absorption members 250. The vibration absorption members 250 can increase the ease of use by decreasing vibrations transmitted from the ultrasound transmission member 230 through the housing 208. The sonic connector 252 can facilitate the coupling of the ultrasound transmission member 230 to an ultrasound transducer device 126. The ultrasound transmission member 230 may extend distally from the sonic connector 252, through the inner cavity 244, Y-connector 216, catheter body 204, and drug delivery balloon 200, terminating at the distal tip 201.

Additional details of ultrasound systems and devices that include ultrasound transmission members (and their distal tips), ultra-sound transducers, sonic connectors and their connections to ultrasound devices are disclosed in U.S. Pat. Nos. 6,007,514, 6,427,118; 6,702,748; 6,855,123; 6,942, 620; 6,942,677; 7,137,963; 7,220,233; 7,297,131; 7,335, 180; 7,393,338; 7,540,852, 7,604,608 and in U.S. Pat. Pub. Nos. 2008/0108937, 2008/0287804, 2010/0317973, the disclosures of which are hereby incorporated by reference in their entireties.

Continuing with FIG. 2B, the sidearm 132 may include a lumen 232 in fluid communication with a lumen 223 in the Y-connector 123. The lumen 223 in the Y-connector 123 can be in fluid communication with a lumen extending through the catheter body 204. Thus, fluid introduced into the sidearm 132 may flow into and through the catheter body 204 and contact the ultrasound transmission member 230. The fluid may flow out of the catheter body 204 through apertures in the distal portions (not shown) or through any other suitable apertures or openings, such as apertures located in the catheter body 204 itself. The fluid may also through the catheter body 204 and into and out of the drug delivery balloon 200.

Any suitable fluid may be passed through the sidearm 132 and the catheter body 204 and into the drug delivery balloon 200. Suitable fluids include, for example, refrigerated fluids, lubricious fluids, super-saturated saline or contrast/saline mixtures, or the like. Cooling and/or lubricating the ultrasound transmission member 230 and support wires 320 in the drug delivery balloon 200 may reduce friction and/or wear and tear of the ultrasound transmission member 230, thus prolonging the ultrasound transmission member's useful life and enhancing overall performance.

The drug delivery balloon 200 may be coupled to the distal portion 121 of the ultrasound device 120. The drug delivery balloon 200 may include a distal tip 201 and a drug-coated balloon wall 300. The distal tip 201 may include a guidewire lumen. In some embodiments, the distal tip 201 is configured to penetrate and/or cross a total occlusion.

As shown in FIG. 2B, the drug delivery balloon 200 includes a drug-coated balloon wall 300 and support wires 320 joined distally and proximally to the ultrasound transmission member 230 at junctions 325 and 322 respectively. The drug delivery balloon 200 may be any suitable size or shape and include any number of support wires 320.

The drug-coated balloon wall 300 can be made from materials such as Nylon, Pebax, PET, Polyurethane and other similar materials known in the art. An exterior surface of the drug-coated balloon wall 300 may include at least one active ingredient and/or therapeutic. In some embodiments, the active ingredient is a drug effective to help prevent re-stenosis. In some embodiments the exterior surface of the drug-coated balloon wall 300 is hydrophilic or made hydrophilic by treatment with a hydrophilizing agent. The exterior surface of drug-coated balloon wall 300 may also include one or more excipients and/or enhancers. Methods known in the art can be used to coat at least a portion of the exterior surface of the drug-coated balloon wall 300 and/or the entire exterior surface the drug-coated balloon wall 300.

Any suitable drug may be included on the drug-coated balloon wall 300. Such drugs may include anti-stenosis or anti-proliferation drugs such as sirolimus, paclitaxel, zotarolimus, everolimus, Biolimus A9 and the like.

The support wires 320 and the ultrasound transmission member 230 may be formed of any material capable of effectively transmitting ultrasonic energy from the ultrasound transducer to the distal end 201 of the ultrasound transmission member 230. These materials include, but are not limited to, metals such as pure titanium or aluminum, or titanium or aluminum alloys, such as NiTi.

The ultrasound transmission member 230 may include one or more tapered regions and/or steps. The tapered regions and steps may increase and/or decrease in width or diameter along the length of the ultrasound transmission member 230 in the distal direction. In one embodiment, the ultrasound transmission member 230 includes at least one portion tapered in a direction extending distally from the proximal end. In another embodiment, the ultrasound transmission member 230 is continuously tapered in a direction extending distally from the proximal end. In one embodiment, the ultrasound transmission member 230 tapers in diameter from about 800 µm proximally, to about 200 µm distally.

In some embodiments, the ultrasound transmission member 230, wire, or wave guide extends longitudinally through a lumen of the catheter body 204. Ultrasonic energy can travel through the ultrasound transmission member 230 from an ultrasound transducer 126 connected to the proximal end of housing 208 to the distal portion of the device. The ultrasound transmission member 230 may operate at frequencies between about 10 Hz to about 20 MHz. In one embodiment, the frequency of vibration is 20 kHz. In one embodiment, the frequency of vibration is 17 kHz. The ultrasound transmission member 230 may operate in continuous mode, pulse mode, or combination of both.

Figure 3A:
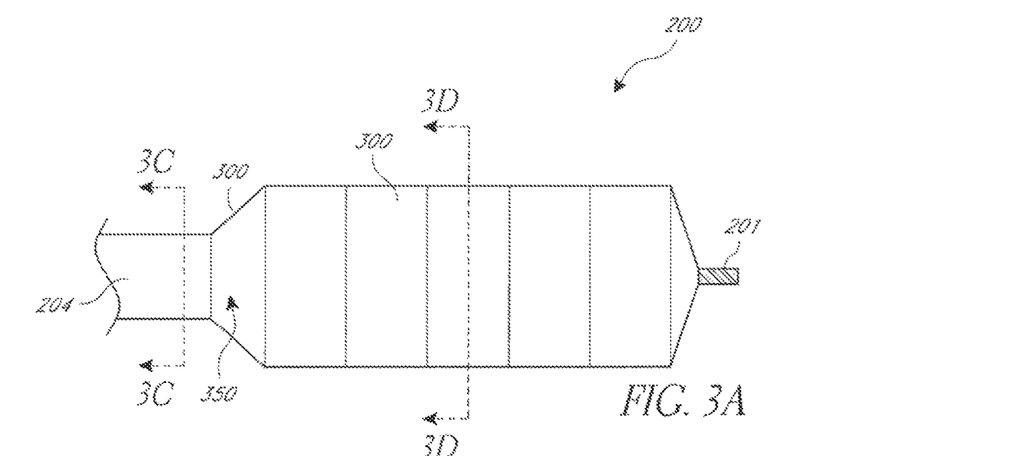
FIG. 3A is an enlarged view of the drug delivery balloon shown in FIG. 2A taken about the line 3A-3A.

FIG. 3A illustrates an inflated drug delivery balloon 200 according to one embodiment. As shown, the catheter body 204 is fused or otherwise bonded to the drug-coated balloon wall 300 at interface 350. In this way, fluid can be delivered through the catheter body 204 and into and out of the drug delivery balloon 200 to inflate and deflate the drug-coated balloon wall 300 as desired.

Figure 3B:
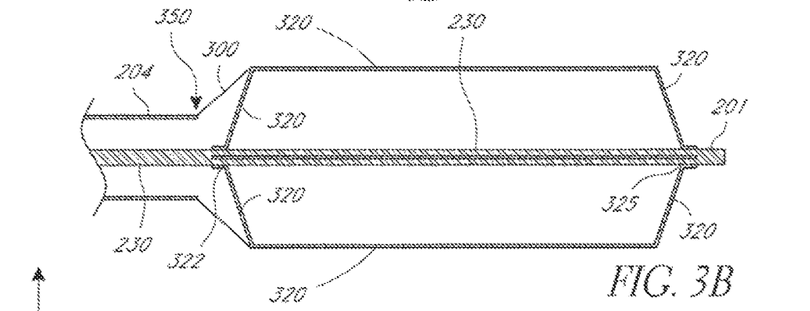
FIG. 3B is an enlarged view of the drug delivery balloon shown in FIG. 2B taken about the line 3B-3B.

FIG. 3B illustrates a cross-section of FIG. 3B and shows support wires 320 joined distally and proximally to the ultrasound transmission member 230 at junctions 325 and 322 respectively. The support wires 320 can be secured to the ultrasound transmission member 230 by soldering, welding, or other mechanical joint.

Figures 3C, 3D:
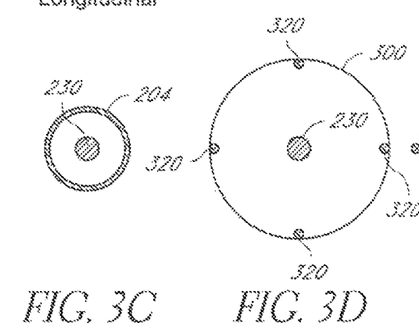
FIG. 3C is a cross-sectional view of the drug delivery balloon shown in FIG. 3A taken along line 3C-3C.
FIG. 3D is a cross-sectional view of the drug delivery balloon shown in FIG. 3A taken along line 3D-3D.
Figure 3D:
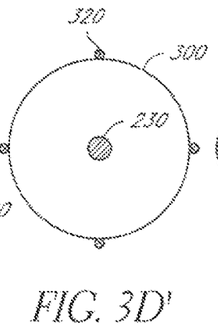
Figure 4A:
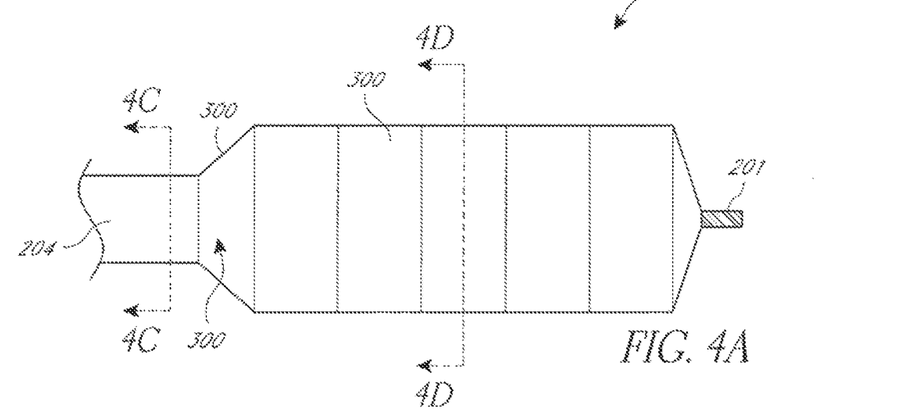
FIG. 4A is an enlarged view of a drug delivery balloon according to another embodiment.
Figure 4B:
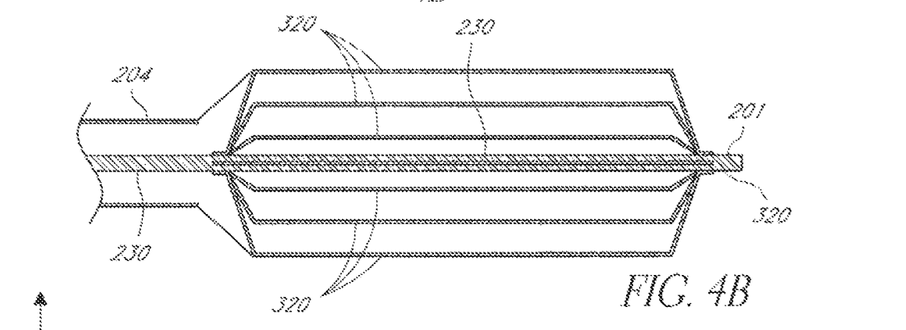
FIG. 4B is a cross-sectional view of the drug delivery balloon shown in FIG. 4A.
Figure 4C:
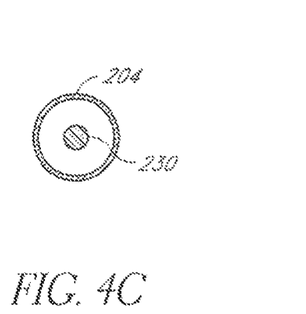
FIG. 4C is a cross-sectional view of the drug delivery balloon shown in FIG. 4A taken along line 4C-4C.
Figure 4D:
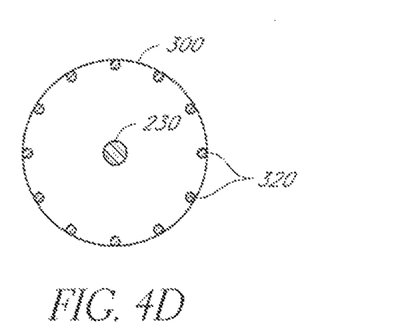
FIG. 4D is a cross-sectional view of the drug delivery balloon shown in FIG. 4A taken along line 4D-4D.

As shown in FIG. 3C, the ultrasound transmission member 230 can pass through the at least one lumen of the catheter body 204. In this way, fluid can be passed through the catheter body 204 and surround the ultrasound transmission member 230 and also enter into the interior of the drug delivery balloon 200. In other embodiments, the catheter body 204 can include additional lumens. For example, the catheter body can include a lumen that surrounds the ultrasound transmission member 230 from, for example, the y-connector to the distal tip 201 of the ultrasound transmission member 230. A separate lumen in the catheter body could then be used as a dedicated inflation/deflation lumen to provide liquid to and from the y-connector and the interior of the drug delivery balloon 200.

Turing to FIG. 3D, it can be seen that the drug delivery balloon 200 includes four support wires 320 positioned on the inner diameter of the drug-coated balloon wall 300. In this way, the support wires contact and are secured to an internal surface of the drug-coated balloon wall 300. However, as shown in FIGS. 3D' and 3D'' in some embodiments, the support wires are located and secured to the outer diameter of the balloon wall, as in FIG. 3D', or embedded within the balloon material as in FIG. 3D''. In addition, the drug delivery balloon 200 can include more or less than four support wires support wires 320. For example, in the embodiment shown in FIGS. 4A-4D, the drug delivery balloon 400 has twelve support wires 320 spaced evenly apart around the inner diameter of the drug-coated balloon wall 300.

Figure 5A:
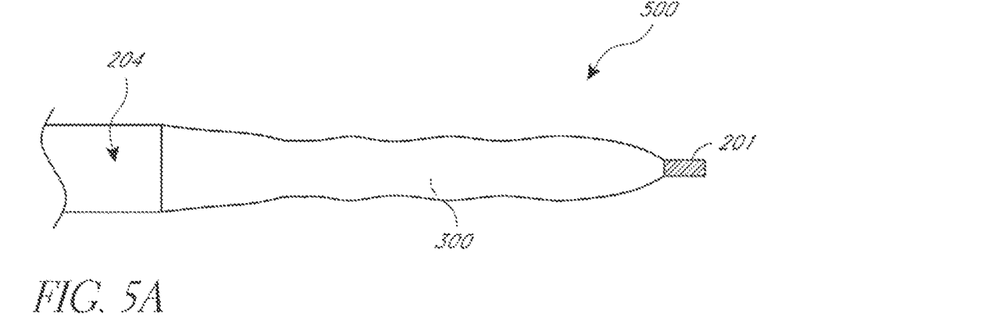
FIG. 5A is an enlarged view of the drug delivery balloon in a deflated state according to one embodiment.

FIG. 5A illustrates a deflated drug delivery balloon 500 according to one embodiment. The proximal end of the drug-coated balloon wall 300 is fused or otherwise bonded to the distal end of the catheter body 204. The distal end of the drug-coated balloon wall 300 is fused or otherwise bonded near to the distal end 201 of the ultrasound transmission member 230.

Figure 5B:
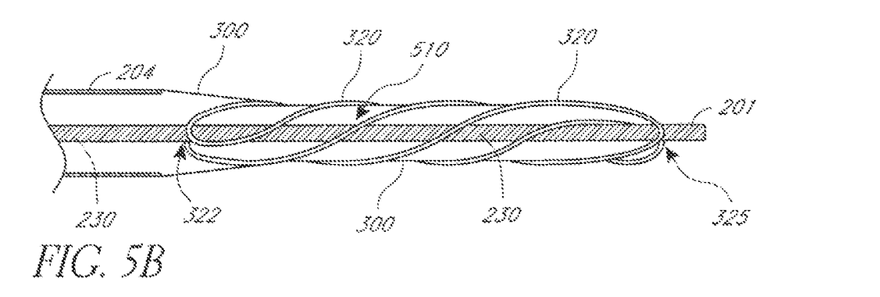
FIG. 5B is a cross-sectional view of the drug delivery balloon shown in FIG. 5A.
Figure 5C:
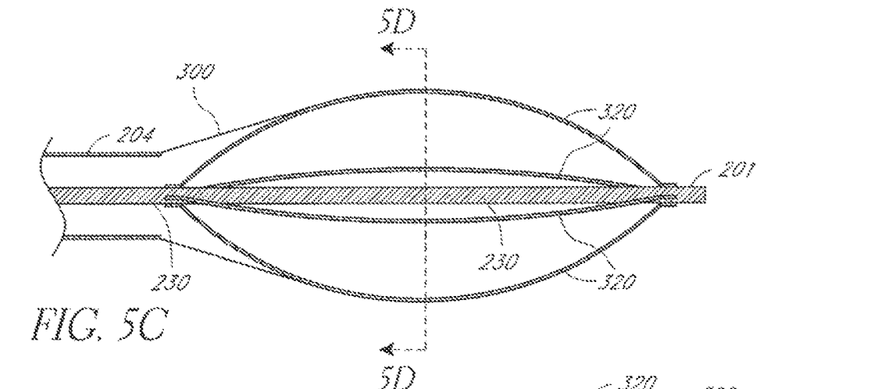
FIG. 5C is a cross-sectional view of the delivery balloon shown in FIG. 5B in an inflated state.
Figure 5D:
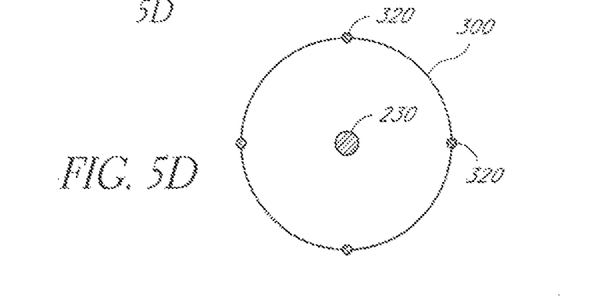
FIG. 5D is a cross-sectional view of the drug delivery balloon shown in FIG. 5C taken along line 5D-5D.

As shown in FIG. 5B, in one embodiment, support wires 320 may be joined proximally and distally to the ultrasound transmission member 230 at a proximal joint 322 and a distal joint 325. In this embodiment, four support wires 320 are twisted over and around the ultrasound transmission member 230 and embedded within the drug-coated balloon wall 300. The catheter body 204 may be in fluid communication with the balloon cavity 510. As the pressure within the balloon cavity 510 rises, the four support wires 320 can unravel and expand with the drug-coated balloon wall 300 as shown in FIG. 5C.

FIGS. 6A-6D illustrate the steps of an exemplary use of the drug delivery balloon 900 configured to be mechanically vibrated in a therapeutic procedure. FIG. 6 illustrates a longitudinal cross-sectional view of an artery 600 having a partial arterial occlusion 650. The occlusion 650 may consist of atheroma, thrombus, plaque, calcific material, or combinations of thereof. For illustrative purposes, a partial arterial occlusion 650 is shown in connection with the device and method described with respect to FIGS. 6A-6D. However, all the devices and methods described herein can also apply to occlusions within veins. Further, although the drug delivery balloon will be shown and described for use in and about an artery, the device may also be used in other blood vessels including veins and capillaries or in other tubular channels, for example channels of the lymphatic system. The device may also be used with total arterial or venous occlusions as well.

Figure 6A:
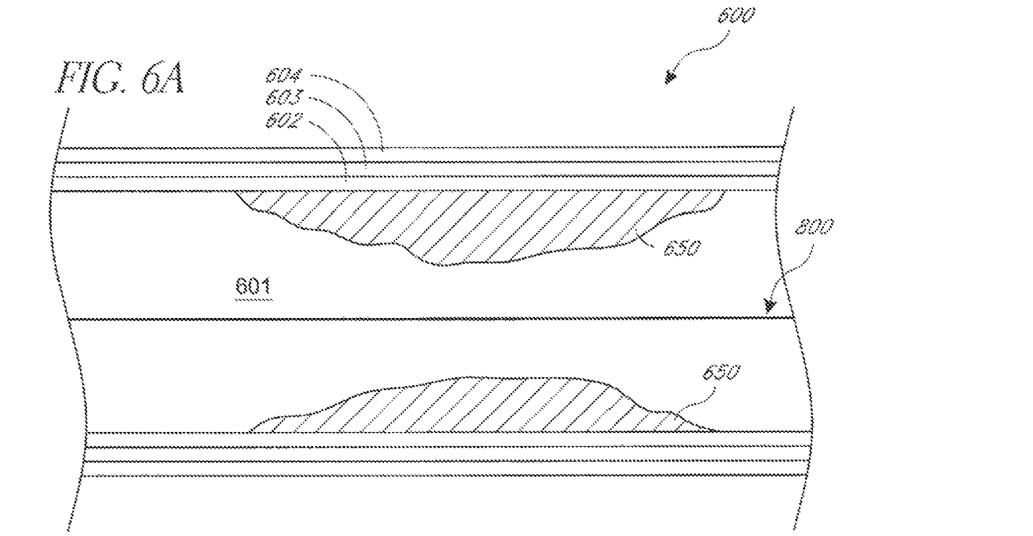
FIG. 6A shows a longitudinal cross-sectional view of a guidewire positioned in a partially occluded artery.

As illustrated in FIG. 6A, a partial arterial occlusion 650 occupies a portion of the lumen, thus blocking blood flow. It is desirable to open such an occlusion, restoring blood flow through affected areas, and thus improving blood supply and heart function. The artery has a central lumen 601 and arterial wall with three layers: the intima 602, the intermedia 603, and the adventitia 604. All three layers consist of elastic tissue, smooth muscle and connecting tissue (collagen). The tissue of the arterial wall is often called a subintimal space. The area outside the adventitia, an external layer of the artery, is called a space outside of the vessel. As shown, in one implementation, a method of using the drug delivery balloon 900a can begin by positioning a guidewire 800 in the central lumen 601.

Figure 6B:
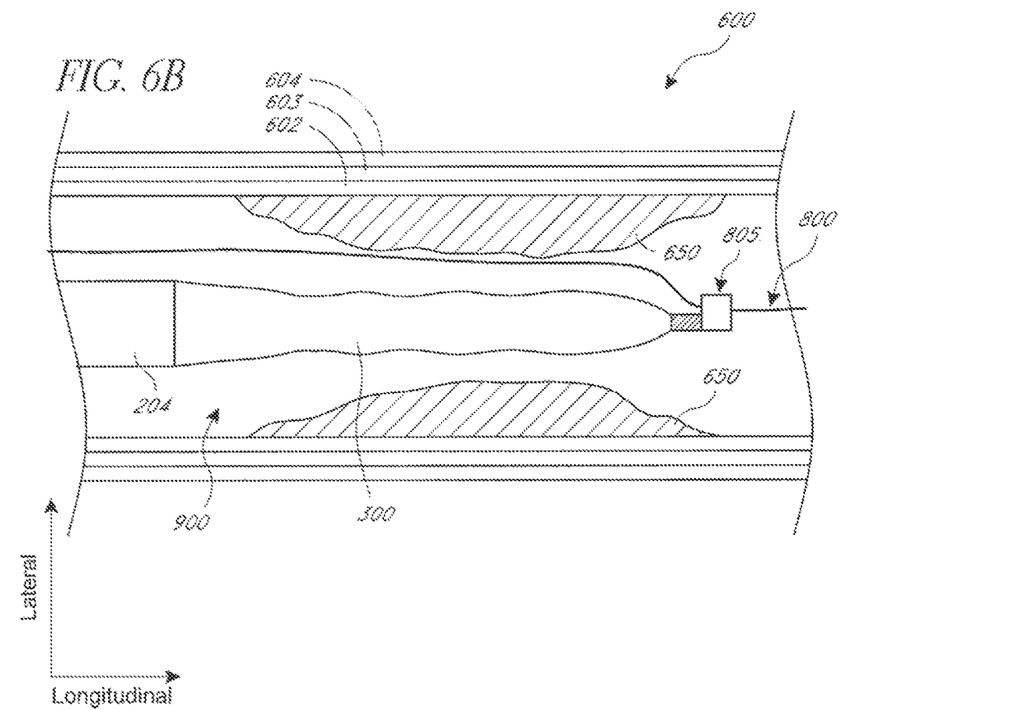
FIG. 6B shows a longitudinal cross-sectional view of the drug delivery balloon positioned in the partially occluded artery of FIG. 6A.

The method can continue as shown in FIG. 6B by threading the drug delivery balloon 900 over the guidewire 801 to reach a target location. The target location may include an arterial partial occlusion 650. In this embodiment, the drug delivery balloon 900 includes a short guidewire lumen 805 located at the distal end of the drug delivery balloon 900. The drug delivery balloon 900 includes a catheter body 204 and a drug-coated balloon wall 300. The drug-coated balloon wall 300 includes at least one support wire 320 imbedded within the drug-coated balloon wall 300. An ultrasound transmission member 230 passes through the catheter body 204 and is connected with at least one support wire 320 imbedded within the drug-coated balloon wall 300.

The catheter body 204, ultrasound transmission member 230, and/or support wires 320 imbedded within the drug-coated balloon wall 300 may include one or more visualization markers. In some embodiments, the visualization markers include radiopaque markers. The visualization markers can help determine the position and orientation of the drug delivery balloon 900.

Figure 6C:
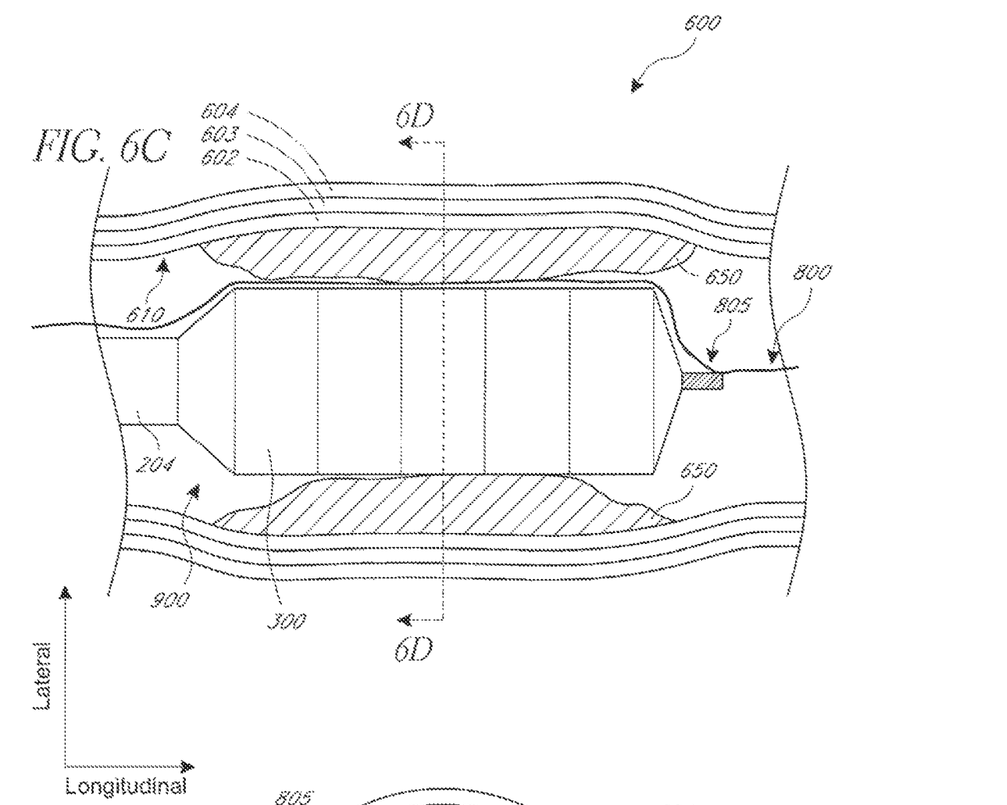
FIG. 6C shows a longitudinal cross-sectional view of the drug delivery balloon shown in FIG. 6B in a partially inflated state.
Figure 6D:
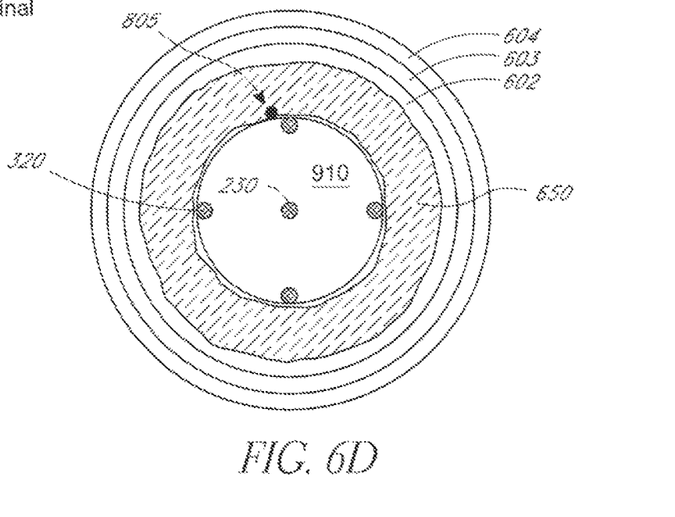
FIG. 6D shows a lateral cross-sectional view of the drug delivery balloon shown in FIG. 6C taken along line 6D-6D.

The method can continue as shown in FIGS. 6C and 6D. As shown, once the drug delivery balloon 900 is positioned in the target location (i.e. positioned within the central lumen and over the partial arterial occlusion 650), the drug delivery balloon 900 is inflated. As discussed above, the drug delivery balloon 900 can be inflated by injecting liquid through an inflation port on the ultrasound device. The liquid can then flow through the catheter body 204 and into the balloon interior. The drug-coated balloon wall 300 can thus be made to contact a surface of the partial arterial occlusion 650 and/or the interior vessel wall 610.

The method continues by applying ultrasonic vibrations to the drug delivery balloon 900. In one embodiment, the system 100 of FIG. 1 is utilized. In this embodiment, a user activates the system 100 by depressing the footswitch 128. Next, the signal generator 127 sends electrical signals to the ultrasound transducer 126. The ultrasound transducer 126 then convert the electrical signals to ultrasonic vibrations. The ultrasonic vibrations are the transmitted through the ultrasound transmission member 230 to the drug delivery balloon 900.

In some embodiments, the ultrasound transmission member 230 vibrates longitudinally. The one or more support wires 320 imbedded within the drug-coated balloon wall 300, coupled to the ultrasound transmission member 230, thus vibrate longitudinally as well. The relatively thin support wires 320, in comparison to the relatively thick ultrasound transmission member 230, can communicate high frequency vibrations across the surface of the drug-coated balloon wall 300. Thus, the inflated drug-coated balloon wall 300 can vibrate longitudinally while contacting the partial arterial occlusion 650 and/or the interior vessel wall 610. In this way, the drug can be physically rubbed off of the drug-coated balloon wall 300. In addition, the high frequency vibration can cause the drug to enter the layers of the vessel wall (i.e. the intima 602, the intermedia 603, and/or the adventitia 604). The ultrasonic vibrations may also cause cavitational effects which may also increase the amount of drug delivered to the interior of the vessel walls.

In some embodiments, when ultrasound energy travels through the ultrasound device and to the drug delivery balloon 900 there is an initial period of time during which the drug delivery balloon 900 vibrates in a more random and aggressive manner than during later time periods in the same activation cycle. After the initial period of time, the drug delivery balloon 900 settles into a steady state. In other words, when the ultrasonic energy first arrives at the drug delivery balloon 900, the longitudinal vibration may be initial absorbed while high frequency vibrations are transmitted to the support wires 320 and drug-coated balloon wall 300, thus vibrating or "shocking" the drug off of the balloon. As such, in some embodiments, the ultrasonic energy is provided in a pulsed or "on-off" manner. For example, in some embodiments, ultrasonic energy is delivered for short periods of time, followed by short periods of inactivation. In some embodiments, ultrasonic energy is delivered for a maximum of 5 minutes with automatic time-outs every 30 seconds.

As shown in FIG. 6D, the drug delivery balloon 900 includes four support wires 320. As the pressure in the interior 910 of the drug delivery balloon 900 increases, the drug-coated balloon wall 300 expands and at least a portion of the outer surface of the drug-coated balloon 300 contacts the partial arterial occlusion 650. As shown, the partial arterial occlusion 650 is located around the entire diameter of the vessel lumen. However, the partial arterial occlusion 650 may not be present around the entire diameter such that at least a portion of the outer surface of the drug-coated balloon wall 300 may contact the internal surface of the vessel wall. In addition, as the pressure in the interior 910 of the drug delivery balloon 900 increases the support wires 320 may exert focused forces on the partial arterial occlusion 650. Such forces may modify, penetrate, and/or crack the partial arterial occlusion 650. When the drug delivery balloon 900 is vibrated, the vibrating support wires 320 may also further modify, penetrate, and/or crack the partial arterial occlusion 650.

After ultrasound vibration is applied to the drug delivery balloon 900; the drug delivery balloon 900 may be deflated and removed. Fluid can be removed from the interior of the balloon and out through the catheter body 204. In some embodiments, a stent is placed in the vessel.

Figure 7:
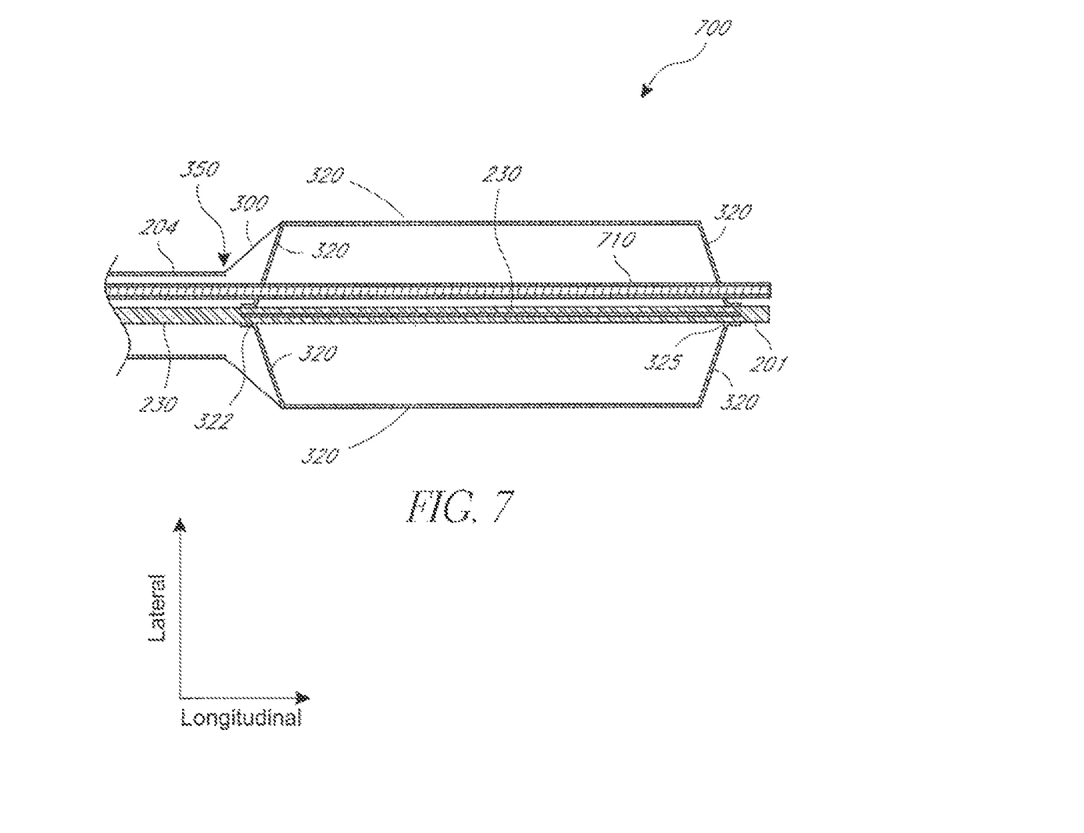
FIG. 7 a cross-sectional view of the drug delivery balloon according to an embodiment that includes an internal guidewire lumen.

Turning to FIG. 7, one embodiment of a drug delivery balloon 700 includes an internal guidewire lumen 710. The internal guidewire lumen 710 may pass through the catheter body 204 and the interior of the balloon. The internal guidewire lumen 710 may then pass out of the balloon. The balloon can be sealed or otherwise bonded to the interface between the guidewire lumen and the balloon. In this way, the internal guidewire lumen 710 can be threaded over the guidewire and positioned in a target location.

The various embodiments described above thus provide a number of ways to provide for treatment of occluded vessels. In addition, the techniques described may be broadly applied for use with a variety of medical procedures. Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Although these techniques and devices have been disclosed in the context of certain embodiments and examples, it will be understood by those skilled in the art that these techniques and devices may be extended beyond the specifically disclosed embodiments to other embodiments and/or uses and obvious modifications and equivalents thereof. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the systems disclosed herein disclosed should not be limited by the particular disclosed embodiments described above, but should be determined only by a fair reading of the claims that follow.

What is claimed is:
1. A drug delivery balloon catheter comprising:
an ultrasound transmission member having a proximal end and a distal end;
a generator configured to provide longitudinal vibrations to the ultrasound transmission member through the proximal end of the ultrasound transmission member coupled to the generator;
a balloon coupled to the distal end of the ultrasound transmission member and being movable between an inflated state and a deflated state; and at least one wire coupled to the ultrasound transmission member and the balloon so as to transmit the longitudinal vibrations parallel to the balloon catheter from the ultrasound transmission member to the balloon such that the balloon is longitudinally vibrated at least when the balloon is in the inflated state.

2. The device of claim 1, further comprising a catheter body having a distal end and at least one lumen extending longitudinally therethrough, the catheter body surrounding at least a portion of the ultrasound transmission member and in fluid connection with the balloon.

3. The device of claim 1, wherein the at least one wire has a proximal end joined to a first location on the ultrasound transmission member and a distal end joined to a second location on the ultrasound transmission member, the second location spaced distally from the first location.

4. The device of claim 3, wherein the first location is proximate a proximal end of the balloon and the second location is proximate a distal end of the device.

5. The device of claim 3, wherein the at least one wire is directly joined to an exterior surface of the ultrasound transmission member at the first location and at the second location.

6. The device of claim 3, wherein the at least one wire is radially distanced from and separated from the ultrasound transmission member between the first location and the second location in the inflated state.

7. The device of claim 1, wherein the device includes four wires coupled to the ultrasound transmission member and contacting a surface of the balloon.

8. The device of claim 1, wherein the device includes twelve wires coupled to the ultrasound transmission member and contacting a surface of the balloon.

9. The device of claim 1, wherein the at least one wire contacts an inner surface of the balloon.

10. The device of claim 1, wherein the at least one wire contacts an outer surface of the balloon.

11. The device of claim 1, wherein the at least one wire is imbedded within the balloon.

12. The device of claim 1, wherein the balloon is coated with at least one therapeutic.

13. The device of claim 12, wherein the at least one therapeutic includes an antistenosis drug.

14. A drug-delivery device for vessels comprising:
a catheter body having at least one lumen extending longitudinally therethrough;
an elongate ultrasound transmission member extending longitudinally through the lumen; and
a drug-coated balloon having at least one support wire coupled to the ultrasound transmission member so as to transmit longitudinal vibrations parallel to the catheter body to the drug-coated balloon such that the drug-coated balloon is longitudinally vibrated.

15. The device of claim 14, wherein the ultrasound transmission member extends longitudinally through the drug-coated balloon.

* * * * *